United States Patent
Iwahori et al.

(10) Patent No.: US 8,176,591 B2
(45) Date of Patent: May 15, 2012

(54) ELECTRICAL TOOTHBRUSH

(75) Inventors: Toshiyuki Iwahori, Mishima-gun (JP); Kota Tomida, Kyoto (JP); Kenji Hashino, Suita (JP); Koji Kurase, Yao (JP)

(73) Assignee: Omron Healthcare Co., Ltd., Kyoto-Shi (JP)

( * ) Notice: Subject to any disclaimer, the term of this patent is extended or adjusted under 35 U.S.C. 154(b) by 0 days.

(21) Appl. No.: 13/227,041

(22) Filed: Sep. 7, 2011

(65) Prior Publication Data

US 2012/0036657 A1     Feb. 16, 2012

Related U.S. Application Data

(63) Continuation of application No. PCT/JP2010/051956, filed on Feb. 10, 2010.

(30) Foreign Application Priority Data

Mar. 17, 2009   (JP) .................. 2009-064274

(51) Int. Cl.
    *A46B 13/02*    (2006.01)
(52) U.S. Cl. ....................................... 15/22.1
(58) Field of Classification Search ............. 15/22.1
    See application file for complete search history.

(56) References Cited

U.S. PATENT DOCUMENTS

| | | | |
|---|---|---|---|
| 5,214,819 A * | 6/1993 | Kirchner | 15/22.1 |
| 5,493,747 A | 2/1996 | Inakagata et al. | |
| 6,536,068 B1 | 3/2003 | Yang et al. | |
| 2007/0190509 A1 | 8/2007 | Kim | |
| 2008/0060148 A1 | 3/2008 | Pinyayev et al. | |
| 2009/0092955 A1 | 4/2009 | Hwang | |
| 2009/0143914 A1 | 6/2009 | Cook et al. | |

FOREIGN PATENT DOCUMENTS

| | | |
|---|---|---|
| JP | A-7-116027 | 5/1995 |
| JP | A-2008-532619 | 8/2008 |
| JP | A-2008-543418 | 12/2008 |
| WO | WO 01/47392 A1 | 7/2001 |
| WO | WO 2006/137648 A1 | 12/2006 |
| WO | WO 2007/097886 A2 | 8/2007 |
| WO | WO 2007/122491 A2 | 11/2007 |
| WO | WO 2009/113491 A1 | 9/2009 |

OTHER PUBLICATIONS

International Search Report dated Mar. 9, 2010 in International Application PCT/JP2010/051956 (with translation).

* cited by examiner

*Primary Examiner* — Randall Chin

(74) *Attorney, Agent, or Firm* — Oliff & Berridge, PLC

(57) ABSTRACT

An electrical toothbrush includes an electrical toothbrush main body including a drive source of a brush; an orientation sensor configured to detect an orientation of the electrical toothbrush main body; and a controller configured to switch an operation mode of the electrical toothbrush according to a result of comparing an orientation value, which is a value calculated from an output of the orientation sensor, and a threshold value set in advance. A threshold value used for switching determination from an operation mode to an operation mode, and a threshold value used for switching determination from the operation mode to the operation mode are set to different values.

8 Claims, 8 Drawing Sheets

(A) Operation mode 1

(B) Operation mode 2

(C) Operation mode 3

(A)

(B)

(A)

(B)

ELECTRICAL TOOTHBRUSH

TECHNICAL FIELD

The present invention relates to an electrical toothbrush.

BACKGROUND ART

There is known an electrical toothbrush of a type in which teeth are brushed (removal of food residue and plaque) by placing a brush that is vibrating or rotating at high speed on the teeth. Recently, a high value added product having the function of being able to switch the operation mode (number of vibrations, vibration pattern, etc.) of the brush has appeared. In such an electrical toothbrush, an appropriate brush angle (angle formed by brush and tooth axis) and an operation mode are recommended to be selected according to the brushing site. For example, when brushing the periodontal pocket (between tooth and gum), the tip of the hair of the brush easily enters the periodontal pocket if the brush is placed at 45 degrees with respect to the tooth axis and thus is effective in removing the plaque. When brushing the side surface (tooth surface) of the tooth, the brush is to be placed at 90 degrees with respect to the tooth axis, and the operation mode in which the stimulation to the gum is small is desirably selected.

In Patent Document 1, there is proposed a method of determining the position and the movement of the brush using an acceleration sensor, an earth magnetic field sensor, and an angular speed sensor, and evaluating the good and bad of the brushing operation of the user.

PRIOR ART DOCUMENT

Patent Document

Patent Document 1: International Publication No. 2006/137648 (Japanese Unexamined Patent Publication No. 2008-543418)

SUMMARY OF THE INVENTION

Problems to be Solved by the Invention

The present inventors are advancing the development of an intelligent electrical toothbrush having a function of detecting an orientation of a toothbrush main body by an orientation sensor, and automatically switching to an appropriate operation mode according to the detection result. The present inventors have found the following problems in the process. For the sake of convenience of the explanation, the problems will be described by using the function of switching to the operation mode suited for the brushing of the periodontal pocket when the brush angle is 45 degrees by way of example.

In the specification of switching to the operation mode for periodontal pocket only when the brush angle is exactly 45 degrees, angle alignment and angle maintaining by a user are difficult. Therefore, in the actual product, control is adopted in which an allowable range of ±10 degrees is given, and when the brush angle is in the range of between 35 degrees and 55 degrees, control of switching to the operation mode for periodontal pocket is adopted. In this case, when the user rotates the toothbrush main body so that the tip of the hair of the brush faces the periodontal pocket, that is, so that the brush angle approaches 45 degrees, the operation mode is switched when the brush angle exceeds 35 degrees (or when brush angle becomes smaller than 55 degrees). In order to continue brushing in the operation mode for periodontal pocket, the user needs to maintain the brush angle within the above range. However, the brush angle sometimes deviates from the above range while changing the brushing position (moving the brush to the periodontal pocket of a different tooth). Furthermore, as the vibration of the drive source (motor or the like) of the brush is superimposed on the sensor output signal as a noise component, the value of the brush angle may fluctuate due to this vibration noise and may deviate from the range. In particular, when the brush angle is around the boundary values (35 degrees, 55 degrees) of the above range, the operation mode is frequently switched and the operation becomes unstable. Moreover, since the operation sound and the vibration transmitted to the hand are frequently changed with the switching of the operation modes, the user may feel an uncomfortable feeling.

The present invention has been made in view of the above problems, and an object thereof is to provide a technique for suppressing the frequent switching of the operation modes caused by the vibration of the drive source or the like in an electrical toothbrush in which the operation mode is automatically switched according to the orientation.

Means for Solving the Problem

In order to achieve the above object, the present invention adopts the following configuration. That is, an electrical toothbrush of the present invention includes an electrical toothbrush main body including a drive source of a brush; an orientation sensor for detecting an orientation of the electrical toothbrush main body; and control means for switching an operation mode of the electrical toothbrush according to a result of comparing an orientation value, which is a value calculated from an output of the orientation sensor, and a threshold value set in advance; wherein a first threshold value used for switching determination from a first operation mode to a second operation mode, and a second threshold value used for switching determination from the second operation mode to the first operation mode are set to different values.

According to such a configuration, a margin (play) corresponding to a difference of the first threshold value and the second threshold value is provided at a boundary of switching of the first operation mode and the second operation mode. This margin causes the fluctuation of the orientation value near the boundary to be absorbed, so that occurrence of frequent switching of the operation modes can be suppressed.

The first threshold value and the second threshold value are preferably set such that a difference becomes greater than a maximum value of a fluctuation width of the orientation value caused by vibration of the drive source. By setting the margin to such a value, the switching of the operation modes caused by the vibration (noise) of the drive source can be prevented as much as possible.

Specifically, the first threshold value is preferably greater than the second threshold value; and the control means preferably switches the first operation mode to the second operation mode when the orientation value exceeds the first threshold value during the first operation mode, and switches the second operation mode to the first operation mode when the orientation value becomes smaller than the second threshold value during the second operation mode.

The first threshold value is preferably greater than the second threshold value; and the control means preferably switches the first operation mode to the second operation mode when a state in which the orientation value exceeds the first threshold value is maintained for a predetermined time during the first operation mode, and switches the second operation mode to the first operation mode when a state in which the orientation value becomes smaller than the second threshold value is maintained for a predetermined time during the second operation mode.

The orientation sensor is preferably an acceleration sensor, and the orientation value is a function of an output value of the acceleration sensor.

Each means and processes described above may be combined with each other as much as possible to configure the present invention.

Effect of the Invention

According to the present invention, there is provided an electrical toothbrush excelling in operability that assists brushing of teeth by an appropriate brush angle.

EMBODIMENT FOR CARRYING OUT THE INVENTION

Hereinafter, preferred embodiments of the present invention will be illustratively described in detail with reference to the drawings.

(Configuration of Electrical Toothbrush)

Figure 1:
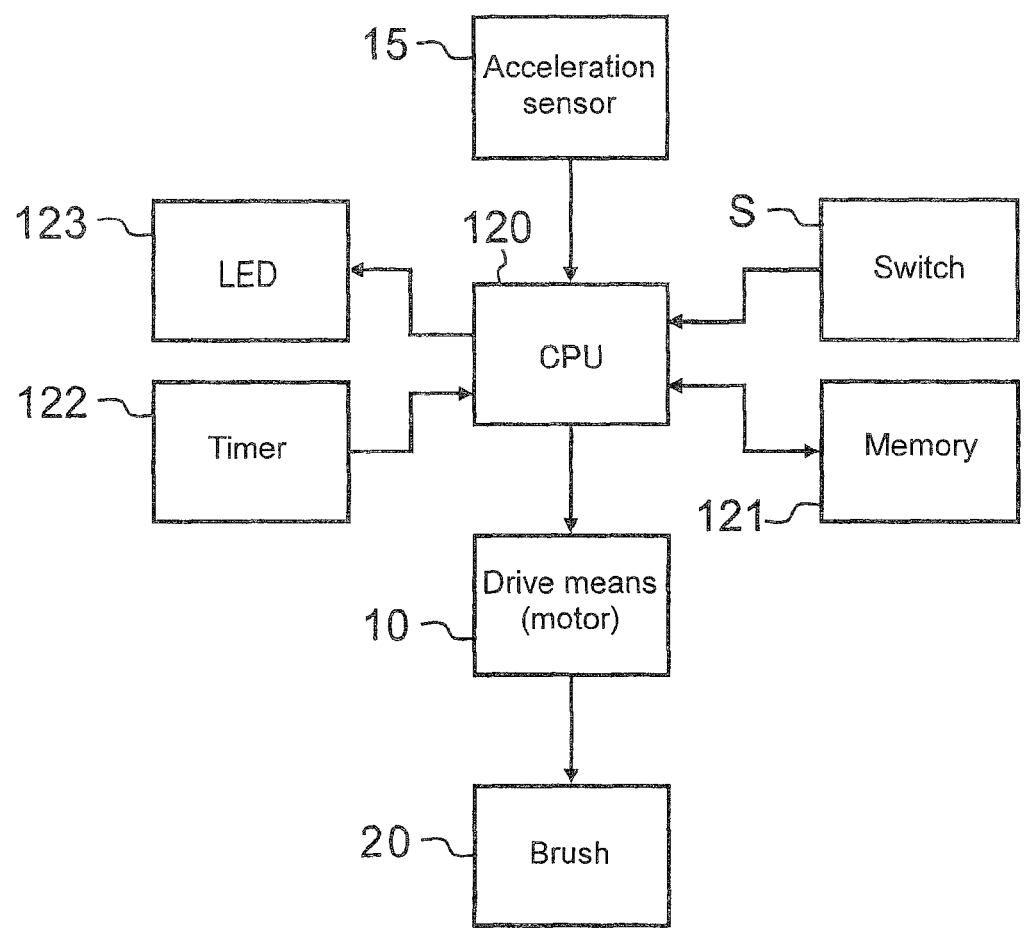
FIG. 1 is a block diagram of an electrical toothbrush.
Figure 2:
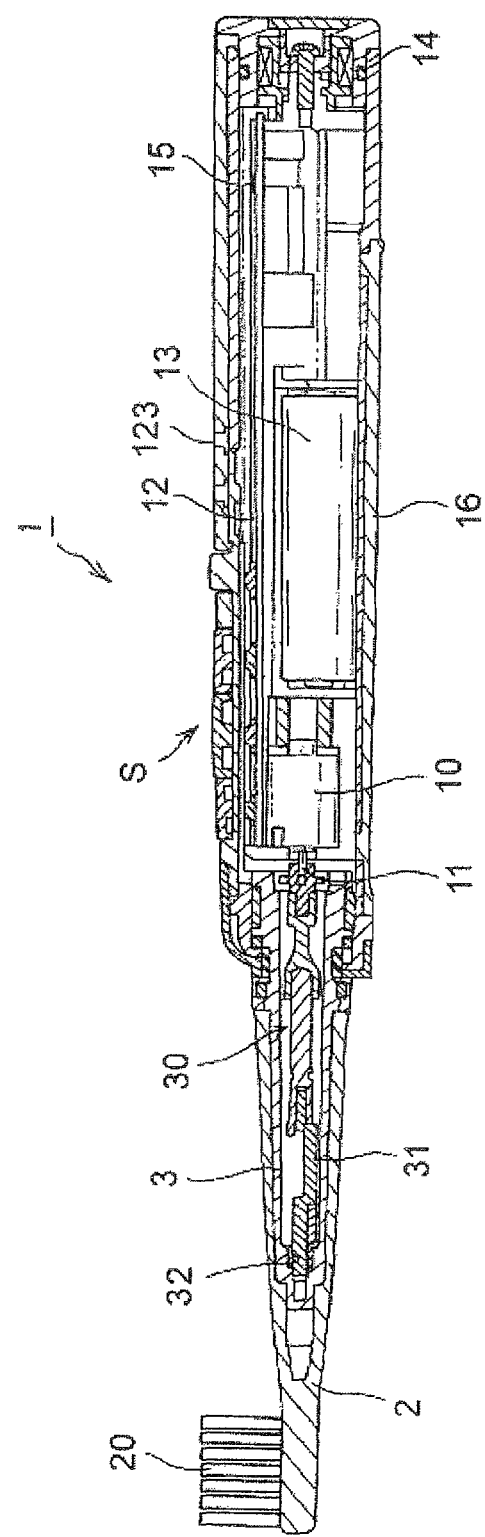
FIG. 2 is a cross-sectional view showing an internal configuration of the electrical toothbrush.
Figure 3:
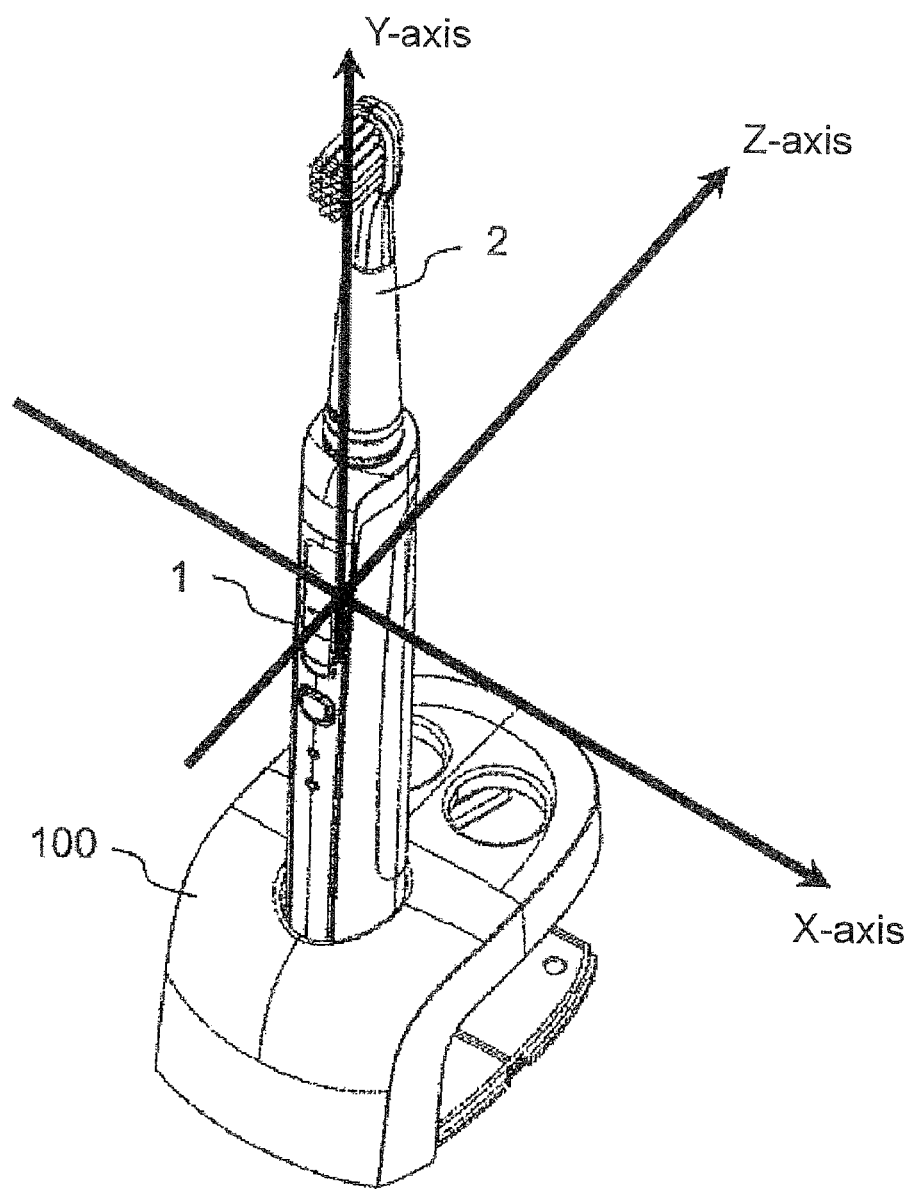
FIG. 3 is a perspective view showing an outer appearance of the electrical toothbrush.

The configuration of the electrical toothbrush will be described with reference to FIG. 1, FIG. 2, and FIG. 3. FIG. 1 is a block diagram of an electrical toothbrush of the present embodiment, FIG. 2 is a cross-sectional view showing an internal configuration of the electrical toothbrush, and FIG. 3 is a perspective view showing an outer appearance of the electrical toothbrush.

The electrical toothbrush includes an electrical toothbrush main body 1 (hereinafter also simply referred to as "main body 1") and a brush member 2 to be attached to the main body 1.

A housing of the main body 1 is made from a resin case that presents a substantially cylindrical shape. The main body 1 includes a grip portion 16, which a user grips with a hand to brush the teeth, a switch S for turning ON/OFF the power and for mode switching, an LED 123, and the like.

A motor 10, which is a drive source, a drive circuit 12, a rechargeable battery 13, which is a 2.4 V power supply, a charging coil 14, and the like are arranged inside the main body 1. When charging the rechargeable battery 13, the main body 1 is simply placed on the charger 100 to enable charging in a non-contact manner through electromagnetic induction. The drive circuit 12 includes a CPU (input and output processing unit) 120 for executing various types of calculations and controls, a memory 121 for storing programs and various types of set values, a timer 122, and the like.

(Acceleration Sensor)

An acceleration sensor 15 serving as an orientation sensor is arranged inside the main body 1. A multi-axial acceleration sensor or a uniaxial acceleration sensor may be used for the acceleration sensor 15. As shown in FIG. 3, in the case of the three-axial acceleration sensor, the x-axis is parallel to the brush surface, the y-axis coincides with the longitudinal direction of the main body 1, and the z-axis is arranged to be perpendicular to the brush surface. The "brush surface" is the virtual plane that is substantially orthogonal to the hair (fiber) of the brush and that is positioned at the distal end portion of the hair. In the case of the uniaxial acceleration sensor, the uniaxial acceleration sensor may be arranged so that the acceleration in the z-axis direction or the x-axis direction in FIG. 3 is detected. In the present embodiment, the three-axial acceleration sensor of x, y, z is used. The output of the acceleration sensor 15 is input to the CPU 120 and used to detect the three-dimensional orientation of the electrical toothbrush.

An MEMS sensor of a piezo resistor type, a capacitance type, or a heat detection type is preferably used for the acceleration sensor 15. This is because the MEMS sensor is very small and can be easily assembled inside the main body 1. However, the form of the acceleration sensor 15 is not limited thereto, and an electrodynamic type, a distortion gauge type, or a piezoelectric type sensor may be used: Although not particularly illustrated, a correction circuit for correcting the balance of the sensitivity of the sensor of each axis, the temperature properties of the sensitivity, the temperature drift and the like may be arranged. A band pass filter (low pass filter) for removing dynamic acceleration components and noise may be arranged, or a filter for removing (reducing) the vibration noise of the motor may be arranged. Furthermore, the noise may be reduced by smoothing the output waveform of the acceleration sensor.

(Drive Mechanism of Brush)

The main body 1 includes a stem 3 arranged to project out from an opening at a distal end side (brush side) of the housing. The brush member 2 is attached so as to cover the stem 3. The brush 20 is implanted at the distal end of the brush member 2. The brush member 2 is a consumable good, and thus is freely attachable and detachable with respect to the stem 3 so that it can be replaced with a new member.

The stem 3 is a tubular member made from a resin material in which the distal end (end on brush side) is closed, and includes a bearing 32 at the distal end of the interior of the tube. A distal end of an eccentric shaft 30 coupled to a rotation shaft 11 of the motor 10 is inserted to the bearing 32 of the stem 3. The eccentric shaft 30 includes a weight 31 in the vicinity of the bearing 32, and the center of gravity of the eccentric shaft 30 is shifted from the center of rotation thereof. When the CPU 120 provides a drive signal (e.g., pulse width modulation signal) corresponding to the operation mode to the motor 10 to rotate the rotation shaft 11 of the motor 10, the eccentric shaft 30 also rotates with the rotation of the rotation shaft 11, but performs a movement of pivoting about the center of rotation since the center of gravity of the eccentric shaft 30 is shifted. Therefore, the distal end of the eccentric shaft 30 repeats microscopic collisions with respect to the inner wall of the bearing 32, which causes the brush 20 to vibrate (move) at high speed. That is, the motor 10 serves as drive means for vibrating (moving) the brush, and the eccentric shaft 30 serves as a motion transmission mechanism (motion conversion mechanism) of converting the output (rotation) of the motor 10 to the vibration of the brush 20.

(Operation of Electrical Toothbrush)

Figure 4:
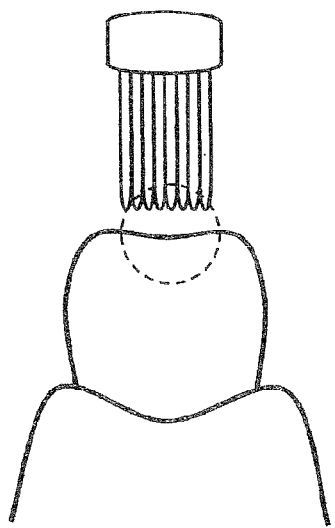
FIGS. 4A to 4C are views describing operation modes.
Figure 4:
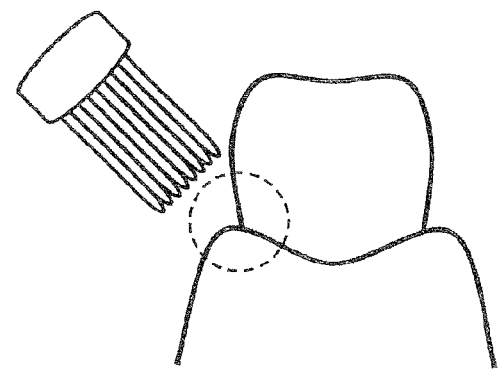
Figure 4:
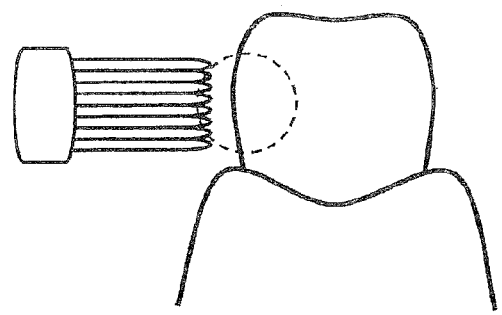

As shown in FIG. 4A, FIG. 4B, and FIG. 4C, the electrical toothbrush of the present embodiment has three operation modes. In such an electrical toothbrush, the orientation (specifically, brush angle) of the toothbrush main body is detected by the acceleration sensor 15, and the mode is automatically switched to an appropriate operation mode according to the value of the brush angle. Note that "spm" is a unit representing the number of swings per minute.

(A) Operation mode 1 (plaque removing mode) . . . Mode suited for brushing of occlusion surface in which highest plaque removing force is obtained. Number of vibrations: about 38000 spm. Brush angle: 0 to 35 degrees.

(B) Operation mode 2 (periodontal pocket mode) . . . Mode suited for brushing of periodontal pocket. Number of vibrations: about 26500 spm. Brush angle: 35 to 55 degrees.

(C) Operation mode 3 (soft mode) . . . Mode suited for brushing of tooth surface in which stimulation on gum is small. Number of vibrations: about 12500 spm. Brush angle: 55 to 90 degrees.

Figure 5:
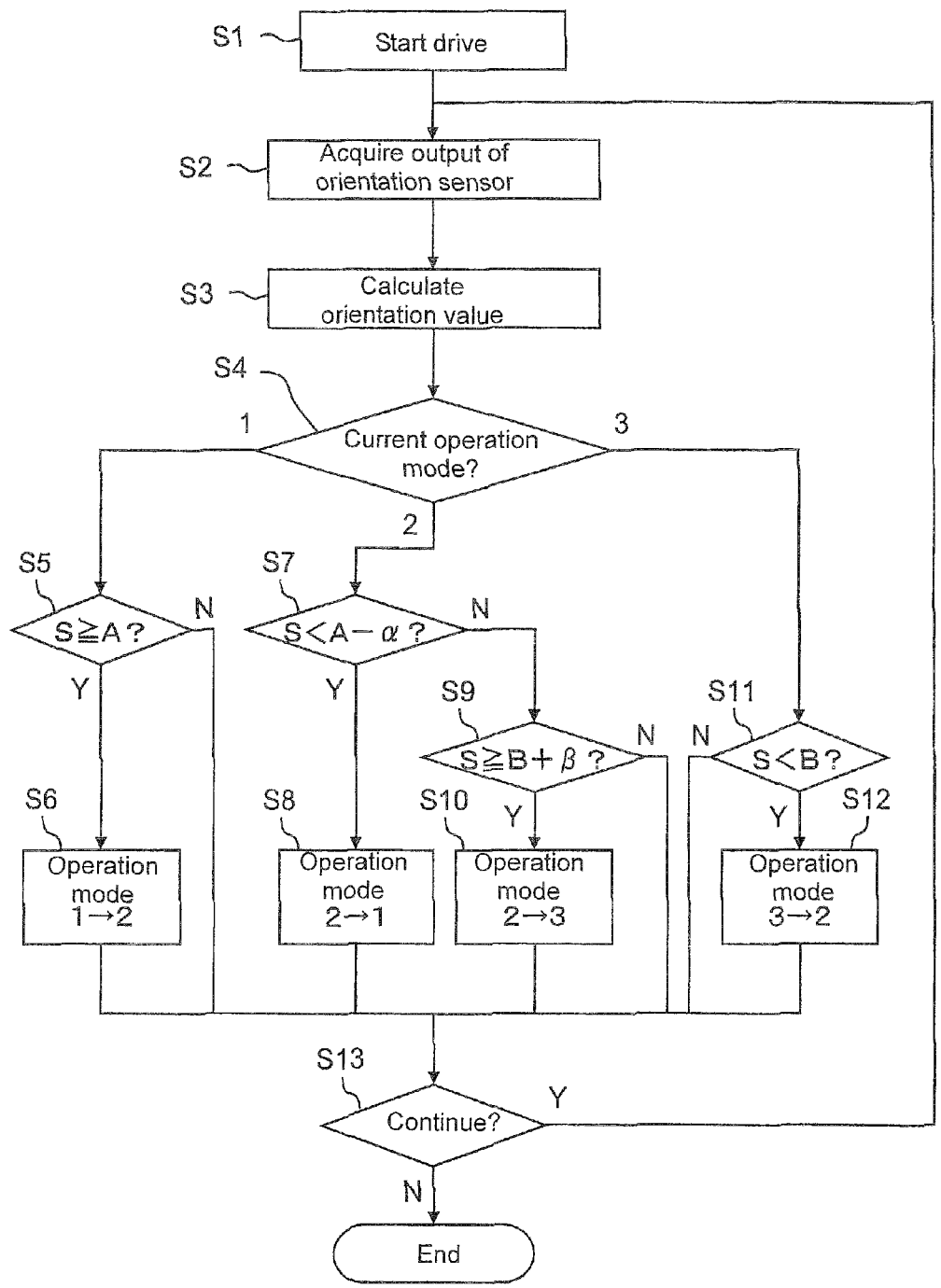
FIG. 5 is a flowchart showing a main routine of the operation of the electrical toothbrush.

FIG. 5 is a flowchart showing the main flow of the electrical toothbrush. The processes described below are processes executed by the CPU 120 according to a program unless particularly stated otherwise.

When the power of the electrical toothbrush is turned ON, the CPU 120 controls the motor 10 to start the drive of the brush 20 (S1). If the operation mode used the previous time is stored in the memory, the drive is started in such an operation mode. The following processes S2 to S13 are repeatedly executed for every constant time. When the power of the electrical toothbrush is turned OFF or the continuous operation time timed by the timer reaches a predetermined time (e.g., two minutes), the loop of S2 to S13 is terminated (S13: NO), and the CPU 120 stops the drive of the brush 20.

Figure 6:
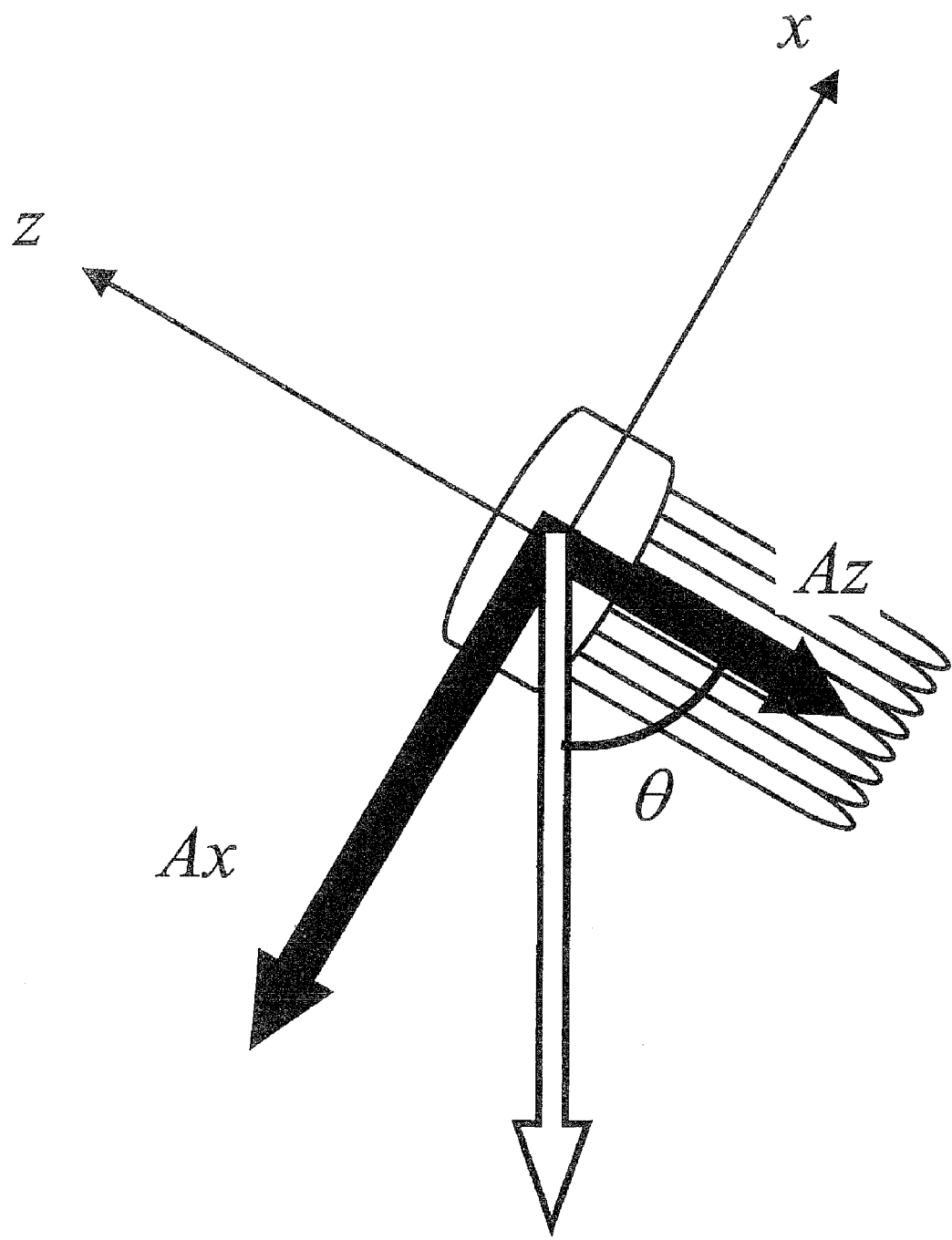
FIG. 6 is a view describing a calculation formula of the brush angle and the orientation value.

The CPU 120 acquires the output of the acceleration sensor 15 in S2 and calculates an orientation value S representing the orientation (brush angle θ) of the toothbrush main body in S3. In the present embodiment, as shown in FIG. 6, the orientation value S is calculated by the following equation assuming the tooth axis is parallel to the gravitational force direction. That is, the orientation value S is a function of an output value Ax of the acceleration sensor in the x-axis direction and an output value Az of the acceleration sensor in the z-axis direction.

Brush angle $\theta = \tan^{-1}(|Ax/Az|)$ orientation value $S = \tan \theta = |Ax/Az|$ The CPU 120 then branches the process according to the current operation mode (S4).

(1) In a case where the current operation mode is "1", the CPU 120 compares the orientation value S and a threshold value A (in this example, A=tan 35 degrees) (S5). If S≧A, that is, if the brush angle exceeds 35 degrees, the operation mode is switched from 1 to 2 (S6). If S<A, that is, if the brush angle is smaller than 35 degrees, the operation mode 1 is continued.

(2) In a case where the current operation mode is "3", the CPU 120 compares the orientation value S and a threshold value B (in this example, B=tan 55 degrees) (S11). If S<B, that is, if the brush angle is smaller than 55 degrees, the operation mode is switched from 3 to 2 (S12). If S≧B, that is, if the brush angle is greater than or equal to 55 degrees, the operation mode 3 is continued.

(3) In a case where the current operation mode is "2", the CPU 120 compares the orientation value S and a threshold value A−α(S7). Here, α is a parameter for differentiating the threshold value (A) used in the switching determination from the operation mode 1 to the operation mode 2, and a threshold value (A−α) used in the switching determination from the operation mode 2 to the operation mode 1, and is set to a value satisfying A−α=tan 34 degrees in this example. In S7, if S<A−α, that is, if the brush angle is smaller than 34 degrees, the CPU 120 switches the operation mode from 2 to 1 (S8). If S≧A−α, that is, if the brush angle is greater than or equal to 34 degrees, the determination of S9 is carried out.

In S9, the CPU 120 compares the orientation value S and a threshold value B+β. Here, β is a parameter for differentiating the threshold value (B+β) used in the switching determination from the operation mode 2 to the operation mode 3, and the threshold value (B) used in the switching determination from the operation mode 3 to the operation mode 2, and is set to a value satisfying B+β=tan 56 degrees in this example. In S9, if S≧B+β, that is, if the brush angle exceeds 56 degrees, the CPU 120 switches the operation mode from 2 to 3 (S10). If S<B+β, that is, if the brush angle is in a range of between 34 degrees and 56 degrees, the operation mode 2 is continued.

(Advantages of Present Embodiment)

As described above, in the electrical toothbrush of the present embodiment, the operation mode is automatically switched to an appropriate operation mode according to the orientation detected with the sensor. In other words, if the brush angle is smaller than about 35 degrees, brushing of the occlusion surface is assumed to be carried out and the operation mode 1 in which the plaque removing force is the highest is selected, and if the brush angle is greater than about 55 degrees, brushing of the tooth surface is assumed to be carried out and the operation mode 3 in which the stimulation to the gum is small is selected. If the brush angle is in a range of about 35 to 55 degrees, the brushing of the periodontal pocket is assumed to be carried out, and the operation mode 2 suited for the brushing of the periodontal pocket is selected. Since the brushing of the periodontal pocket is especially important in preventing a periodontal disease and the like, it is preferable to notify the user that the brush angle is appropriate (about 45 degrees) by lighting the LED 123 or emitting a notification sound during the operation of the operation mode 2.

Figure 7:
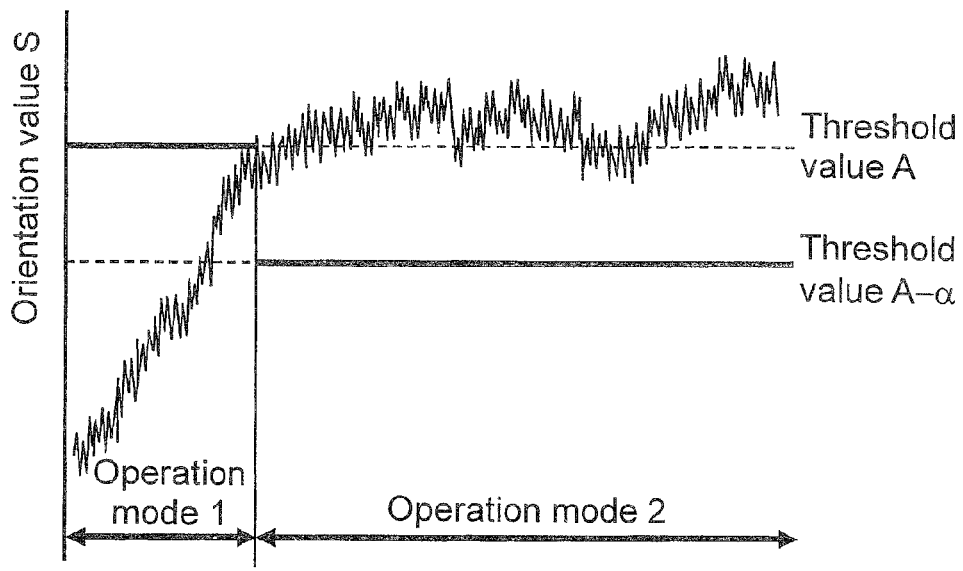
FIG. 7A is a view describing the operation mode switching control of the present embodiment.
FIG. 7B is a view describing a comparative example.
Figure 7:
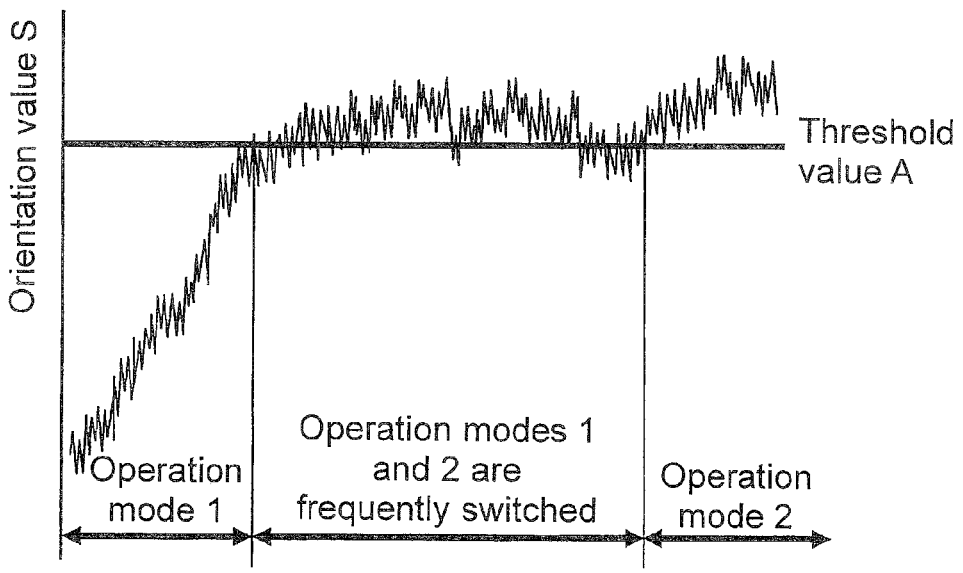

The advantages of the operation mode switching control of the present embodiment will be described with reference to FIG. 7A and FIG. 7B. FIG. 7B shows an example of using a fixed threshold value A for the switching determination between the operation mode 1 and the operation mode 2 as a comparative example. The vertical axis indicates the orientation value S and the horizontal axis indicates the time. First, assume that the orientation value S is smaller than the threshold value A and the electrical toothbrush is driven in the operation mode 1. As the user gradually widens the brush angle from such a state, switching from the operation mode 1 to the operation mode 2 occurs at the time point where the orientation value S reaches the threshold value A. In this case, the orientation value S is to be maintained at a value sufficiently greater than the threshold value A (e.g., 45 degrees), but if the orientation value S is near the threshold value A as shown in FIG. 7B, the magnitude relationship of the orientation value S and the threshold value A is easily inverted, and hence the operation modes 1 and 2 are frequently switched and the operation becomes unstable. In particular, since the electrical toothbrush incorporates a motor, the vibration noise of the motor is superimposed on the output of the acceleration sensor and the fluctuation of the orientation value S is large.

Therefore, in the present embodiment, as shown in FIG. 7A, a margin (play) α is given to the boundary of switching between the operation mode 1 and the operation mode 2 by dynamically changing the threshold value according to the current operation mode. That is, although the switching determination of the operation mode is carried out with the threshold value A during the execution of the operation mode 1, the switching determination is carried out with the threshold value A−α after the orientation value S exceeds the threshold value A and the switching to the operation mode 2 is made. Therefore, even if the orientation value S fluctuates near the threshold value A as shown in FIG. 7A, the fluctuation thereof is absorbed by the margin α and the occurrence of frequent switching of the operation modes is suppressed. The occurrence of frequent switching of the operation modes is similarly suppressed by the margin β in the switching control between the operation modes 2 and 3.

In the embodiment described above, the margin of one degree is provided when converted to the brush angle, but the value of the margin is not limited thereto. The margins α, β are preferably set to values greater than the maximum value of the fluctuation width of the orientation value S caused by the vibration of the motor (drive source). This is because the switching of the operation modes caused by the vibration of the drive source can be prevented as much as possible. However, if the ensured margin is too large, the sensitivity of switching of the operation modes may degrade and may possibly give an uncomfortable feeling to the user. Therefore, the value of the margin is preferably smaller than half of the numerical value range of one operation mode, and is more preferably smaller than ten degrees when converted to the brush angle for practical purposes.

Figure 8:
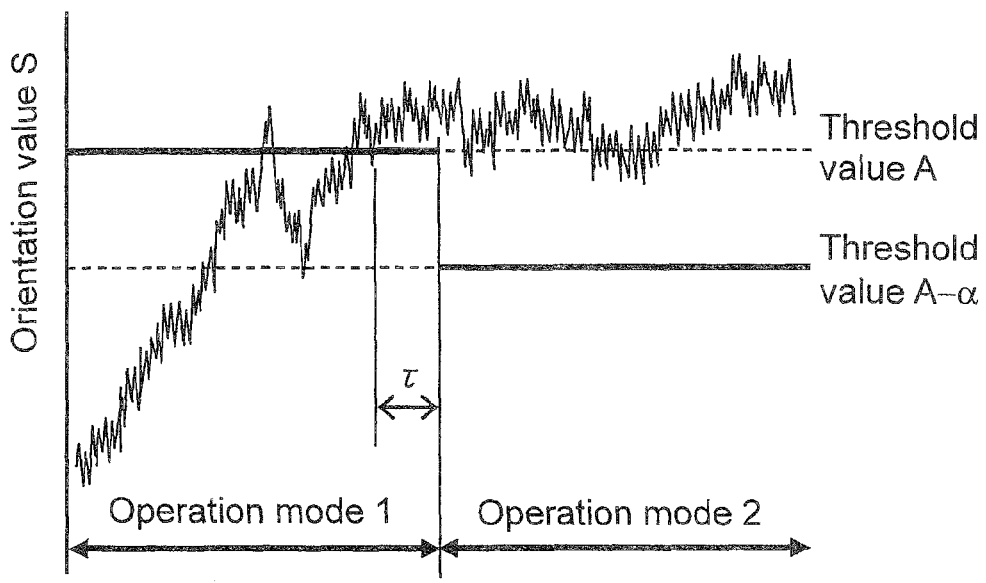
FIG. 8A is a view describing a variant of the operation mode switching control of the present embodiment.
FIG. 8B is a view describing a comparative example.
Figure 8:
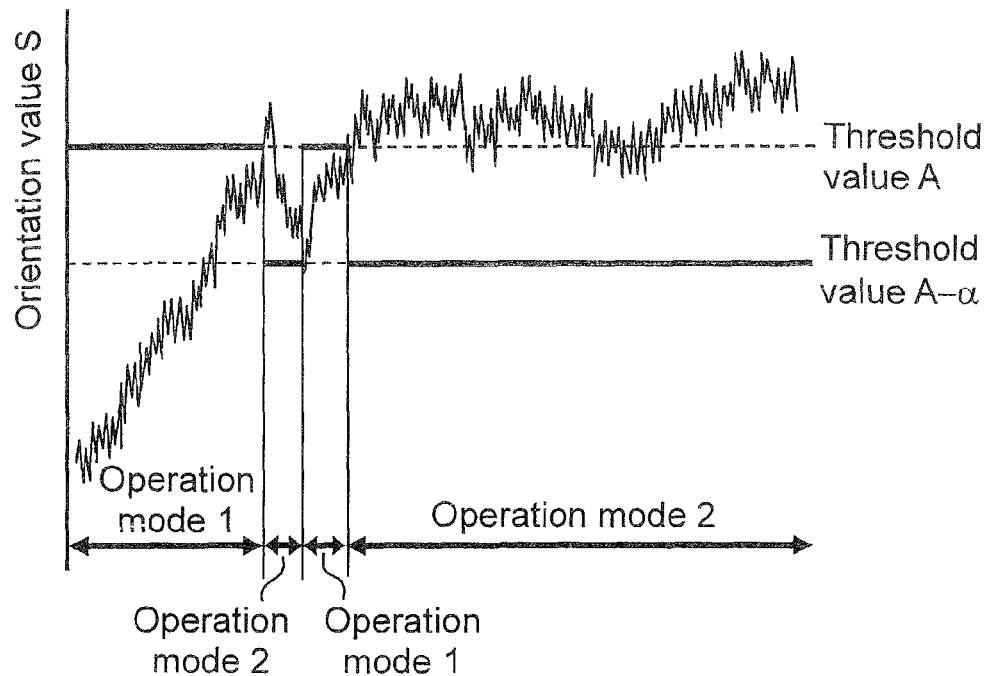

If the orientation value S rapidly changes near the threshold value A as shown in FIG. 8B, the frequent switching of the operation modes may occur even if the threshold value is changed as in the embodiment described above. For example, if the user reflexively stops the hand or returns the brush angle when the operation mode is switched, there is a possibility such a rapid change may appear. Here, instead of immediately switching the operation mode when the orientation value S exceeds the threshold value A, the operation mode may be switched only if the state in which the orientation value S exceeds the threshold value A is maintained for a predetermined time τ(e.g., τ=250 msec), as shown in FIG. 8A. The frequent switching of the operation modes is further suppressed by such switching control. Similar time may be set for the switching from the operation mode 2 to 1, or switching from the operation mode 2 to 3 as well as 3 to 2.

(Others)

The configuration of the embodiment described above merely illustrates one specific example of the present invention. The scope of the invention is not limited to such an embodiment, and various modifications may be made within the scope of the technical idea. For example, the electrical toothbrush of vibration method by the eccentric weight has been described in the embodiment described above, but the present invention is also applicable to the electrical toothbrush of other motion systems. For example, the present invention is applicable even to the electrical toothbrush combining rotation reciprocating motion, linear reciprocating motion, brush hair rotating motion, or a combination thereof. The present invention is also applicable to the electrical toothbrush of not the charging type but a battery type or a type used by connecting a power supply cord.

The number and the content of the operation mode are not limited to the example of the embodiment described above. The number of the operation modes may be two, or more than three. Other than switching the vibration number (number of rotations of motor), the motion system, the motion direction, or the like of the brush may be switched for every operation mode. In any case, the frequent switching of the operation modes can be suppressed by applying the present invention to the switching determination between adjacent operation modes. The threshold values and the values of the margin can be arbitrarily set according to the product specification.

The calculation equation of the orientation value S is not limited to the example of the embodiment described above. For example, the orientation value S corresponding to the brush angle θ may be calculated from only the acceleration component Ax in the x direction or the acceleration component Az in the z direction. The orientation value S can be more accurately calculated by also taking into consideration the acceleration component Ay in the y direction in addition to Ax and Az. In the embodiment described above, the brush angle is taken into consideration for the orientation of the toothbrush main body, but the brushing position is also preferably taken into consideration. The orientation value S in this case has a value corresponding to the brushing position or both the brushing position and the brush angle. In other words, any scale may be adopted for the orientation value S as long as it is a scale that directly or indirectly represents the orientation of the toothbrush main body. As the orientation sensor for detecting the orientation of the toothbrush main body, a rotary sensor, an inclination sensor, a gyroscope, and the like may be used in addition to the acceleration sensor. The orientation may be more accurately detected by preferably combining a plurality of types of sensors.

The invention claimed is:

1. An electrical toothbrush comprising:
an electrical toothbrush main body including a drive source of a brush;
an orientation sensor configured to detect an orientation of the electrical toothbrush main body; and
a controller configured to switch an operation mode of the electrical toothbrush according to a result of comparing an orientation value, which is a value calculated from an output of the orientation sensor, and a threshold value set in advance; wherein
a first threshold value used for switching determination from a first operation mode to a second operation mode, and a second threshold value used for switching determination from the second operation mode to the first operation mode are set to different values.

2. The electrical toothbrush according to claim 1, wherein the first threshold value and the second threshold value are set such that a difference thereof becomes greater than a maximum value of a fluctuation width of the orientation value caused by vibration of the drive source.

3. The electrical toothbrush according to claim 2, wherein the orientation sensor is an acceleration sensor, and the orientation value is a function of an output value of the acceleration sensor.

4. The electrical toothbrush according to claim 1, wherein the first threshold value is greater than the second threshold value; and
the controller is configured to switch the first operation mode to the second operation mode when the orientation value exceeds the first threshold value during the first operation mode, and configured to switch the second operation mode to the first operation mode when the orientation value becomes smaller than the second threshold value during the second operation mode.

5. The electrical toothbrush according to claim 4, wherein the orientation sensor is an acceleration sensor, and the orientation value is a function of an output value of the acceleration sensor.

6. The electrical toothbrush according to claim 1, wherein
the first threshold value is greater than the second threshold value; and
the controller is configured to switch the first operation mode to the second operation mode when a state in which the orientation value exceeds the first threshold value is maintained for a predetermined time during the first operation mode, and configured to switch the second operation mode to the first operation mode when a state in which the orientation value becomes smaller than the second threshold value is maintained for a predetermined time during the second operation mode.

7. The electrical toothbrush according to claim 6, wherein the orientation sensor is an acceleration sensor, and the orientation value is a function of an output value of the acceleration sensor.

8. The electrical toothbrush according to claim 1, wherein the orientation sensor is an acceleration sensor, and the orientation value is a function of an output value of the acceleration sensor.

\* \* \* \* \*